United States Patent
Anderson

(10) Patent No.: US 10,153,057 B2
(45) Date of Patent: Dec. 11, 2018

(54) SYSTEM AND METHOD FOR GENERATING AND USING A WEARABLE DEVICE PROFILE

(71) Applicant: Intel Corporation, Santa Clara, CA (US)

(72) Inventor: Glen J. Anderson, Beaverton, OR (US)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 15/617,965

(22) Filed: Jun. 8, 2017

(65) Prior Publication Data

US 2017/0277850 A1 Sep. 28, 2017

Related U.S. Application Data

(63) Continuation of application No. PCT/US2015/058968, filed on Nov. 4, 2015, which is
(Continued)

(51) Int. Cl.
| | |
|---|---|
| *G08B 23/00* | (2006.01) |
| *G16H 40/63* | (2018.01) |
| *H04B 1/3888* | (2015.01) |
| *G06F 19/00* | (2018.01) |
| *A45F 5/00* | (2006.01) |

(Continued)

(52) U.S. Cl.
CPC .............. *G16H 40/63* (2018.01); *G06F 19/00* (2013.01); *H04B 1/385* (2013.01); *H04B 1/3888* (2013.01); *A44C 5/0015* (2013.01); *A45F 2005/008* (2013.01); *H04B 2001/3855* (2013.01); *H04B 2001/3861* (2013.01); *H04M 1/04* (2013.01)

(58) Field of Classification Search
CPC .... G06F 19/3406; H04M 1/04; G05B 13/021; A61B 5/6831
USPC ....... 340/573.4, 573.1, 524, 686.1, 687, 5.1, 340/8.1
See application file for complete search history.

(56) References Cited

U.S. PATENT DOCUMENTS 8,469,862 B2 6/2013 Andren et al.
9,781,984 B2 * 10/2017 Baranski .............. A44C 5/2071
(Continued)

FOREIGN PATENT DOCUMENTS

| KR | 20100002017 | 1/2010 |
| WO | 2014124483 | 8/2014 |

OTHER PUBLICATIONS

International Searching Authority, "International Search Report and Written Opinion," issued in connection with International Patent Application No. PCT/US2015/058968, dated Feb. 23, 2016, 14 pages.
(Continued)

*Primary Examiner* — Toan N Pham
(74) *Attorney, Agent, or Firm* — Hanley, Flight & Zimmerman, LLC

(57) ABSTRACT

A system and method for generating and using a wearable device profile are disclosed. A particular embodiment includes: a retention mechanism including an attachment mechanism configured to attach the retention mechanism to a body part of a user; a memory device for storage of information indicative of the location of the body part in a wearable device profile; and a data interface for communicating the wearable device profile to another electronic device.

20 Claims, 5 Drawing Sheets

Related U.S. Application Data a continuation of application No. 14/563,630, filed on Dec. 8, 2014, now Pat. No. 9,380,855.

(51) Int. Cl.
  *A44C 5/00* (2006.01)
  *H04M 1/04* (2006.01)
  *H04B 1/3827* (2015.01)

(56) References Cited

U.S. PATENT DOCUMENTS

| | | | |
|---|---|---|---|
| 2003/0030561 A1* | 2/2003 | Yafuso | G08B 21/0227 340/573.4 |
| 2008/0054039 A1 | 6/2008 | Wulff et al. | |
| 2014/0139486 A1 | 5/2014 | Mistry et al. | |
| 2014/0218184 A1 | 8/2014 | Grant et al. | |
| 2014/0343372 A1* | 11/2014 | Ahmed | A61B 5/02405 600/301 |
| 2015/0241985 A1* | 8/2015 | Elangovan | G06F 3/017 345/174 |
| 2016/0007925 A1* | 1/2016 | Mirov | A61B 5/0059 356/400 |
| 2017/0043228 A1* | 2/2017 | Hunter | G06K 19/0723 |

OTHER PUBLICATIONS

United States Patent and Trademark Office, "Notice of Allowance and Fee(s) Due," issued in connection with U.S. Appl. No. 14/563,630, dated Feb. 29, 2016, 10 pages.

\* cited by examiner

SYSTEM AND METHOD FOR GENERATING AND USING A WEARABLE DEVICE PROFILE

RELATED APPLICATIONS

This patent arises from continuation of International Application No. PCT/US2015/058968, titled "System and Method for Generating and Using a Wearable Device Profile," filed Nov. 4, 2015, which is a continuation of U.S. application Ser. No. 14/563,630 (now U.S. Pat. No. 9,380,855), titled "System and Method for Generating and Using a Wearable Device Profile," and filed Dec. 8, 2014. The disclosures of International Application No. PCT/US2015/058968 and U.S. application Ser. No. 14/563,630 are incorporated herein by this reference in their entireties.

TECHNICAL FIELD

This patent application relates to electronic systems, wearable devices, mobile devices, and electronic-enabled apparel according to various example embodiments, and more specifically to a system and method for generating and using a wearable device profile.

BACKGROUND

Computing devices, communication devices, imaging devices, electronic devices, accessories, or other types of peripheral devices designed to be worn or attached to a user (denoted as wearables or wearable devices) are becoming very popular. Wearables can be considered to be a form of mobile device. Mobile phones with headsets or earbud accessories, the Google® Glass™ wearable computer, wrist-worn devices, waist or ankle worn devices, and garments with embedded phones or music players are examples of such wearables or mobile devices.

The wearable's device market space is expected to substantially grow in the coming years. A good portion of these devices will be wearable's that are designed directly into or onto an article of clothing; because, the device will need to be connected to a series of sensors that are woven into the clothing itself. Knowing the body area on which a wearable is placed is valuable for many reasons. For example, an estimate of calories burned would be different for the same accelerometer readings from the ankle vs. the wrist. One approach to understanding place of attachment is through analysis of accelerometer readings; however, this requires a sufficient sample of movement. Depending on the exercise or the movement, the analysis may be misinterpreted. Sometimes a device may be used as a wearable and a non-wearable. It could be advantageous for a system to know when a device is being used as a wearable device or attached to a stationary holding mechanism. It is also desirable to have additional ways to allow a system to understand where a given device is attached to a body or to an object.

BRIEF DESCRIPTION OF THE DRAWINGS

The various embodiments are illustrated by way of example, and not by way of limitation, in the figures of the accompanying drawings in which.

DETAILED DESCRIPTION

In In the following description, for purposes of explanation, numerous specific details are set forth in order to provide a thorough understanding of the various embodiments. It will be evident, however, to one of ordinary skill in the art that the various embodiments may be practiced without these specific details.

In the various embodiments described herein, a system and method for generating and using a wearable device profile are disclosed. The various embodiments described herein provide various ways to instrument straps, bands, and/or other mobile device retention mechanisms in such a way that the retention mechanism can obtain and report information about how or where a wearable device is attached to the body of a user or an object. This information obtained and reported by the retention mechanism can be stored in a wearable device profile that can be used to configure the operation of the wearable device, a mobile device, or other electronic devices. For example, a retention mechanism of an embodiment described herein may determine and report that the wearable device associated with or retained by the retention mechanism is currently being worn on a user's wrist. This information, stored in the wearable device profile, can be used by processing logic in the wearable device or in separate devices to infer that an accelerometer, for example, used by the wearable device is positioned on the user's wrist relative to the user's body. This information can be used to adjust the motion parameters of the accelerometer to more accurately compute movement, speed, and position of the user. In a similar manner, the information in the wearable device profile can be used to configure the operation of the wearable device, a mobile device, or other electronic devices. The wearable device, mobile device, other electronic device, or other computing machine may be a personal computer (PC), a laptop computer, a tablet computing system, a Personal Digital Assistant (PDA), a cellular telephone, a smartphone, a web appliance, a fitness device, a medical device, a timing device, a communication device, a recording device, a set-top box (STB), a network router, switch or bridge, or any machine capable of executing a set of instructions (sequential or otherwise) or activating processing logic that specify actions to be taken by that machine. Various example embodiments are described in detail below.

Figure 1:
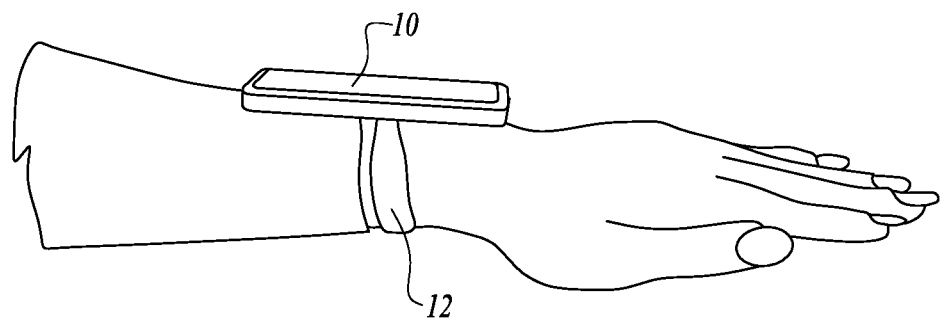
FIGS. 1 and 2 illustrate an example of a same mobile device being worn on two different parts of the body.
Figure 2:
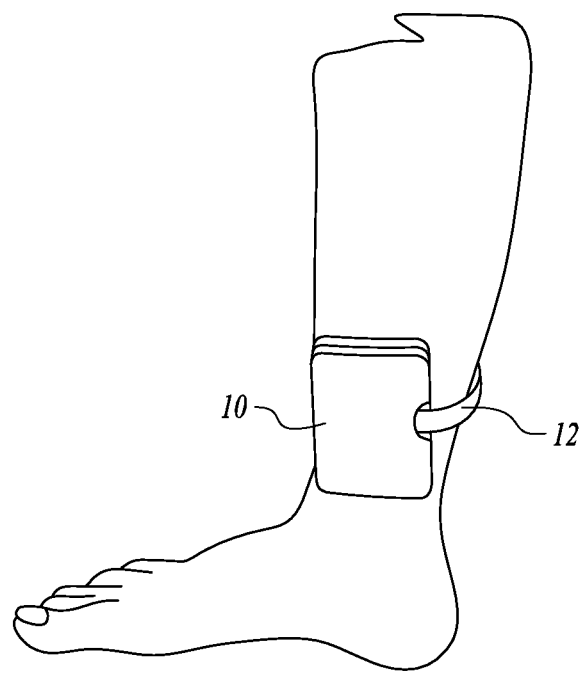

FIGS. 1 and 2 illustrate an example of a same mobile device 10 being worn on two different parts of the body, the wrist of the wearer and the ankle of the wearer. As well-known, the diameter of a typical person's wrist is different than the diameter of the person's ankle. Similarly, the dimensions of other parts of the body have distinctive measurements that enable an example embodiment described herein to differentiate between the different body locations on which a mobile device may be worn or attached. For example, as shown in FIGS. 1 and 2, a strap or band 12 (e.g., a retention mechanism) can be used to attach the mobile device 10 to the wrist or ankle. Because the diameter of a typical person's wrist is typically different than the diameter of the person's ankle, the strap or band 12 would have to attach differently between the wrist and ankle to accommodate the different sizes of these body parts. In particular, the wrist band would likely be attached to a point on the band that forms a smaller circumference relative to the attach point for an ankle band, where the circumference would likely be larger. This difference in the placement of the attach point on the strap/band that is used to adjust the retention mechanism to accommodate different body parts can be used in an example embodiment to associate the adjustment of the retention mechanism with the location on the body or object where the mobile device is being worn. The information corresponding to the adjustment of the retention mechanism can be stored in a wearable device profile and used by the mobile device or other devices to configure or calibrate the operation of the mobile device.

In an example embodiment, the retention mechanism can have memory, a controller, data processor, central processing unit (CPU), or other computing element, and output interface to report the retention mechanism profile to a wearable device that is attached to or associated with the retention mechanism. In a particular embodiment, a strap (e.g., a portion of the retention mechanism) can be instrumented so that the strap measures the circumference of the limb or torso area to which the strap and associated mobile device are attached. This embodiment has the added advantage of enabling an estimation of the size of the person (or the person's limb) wearing the associated mobile device.

Figure 3:
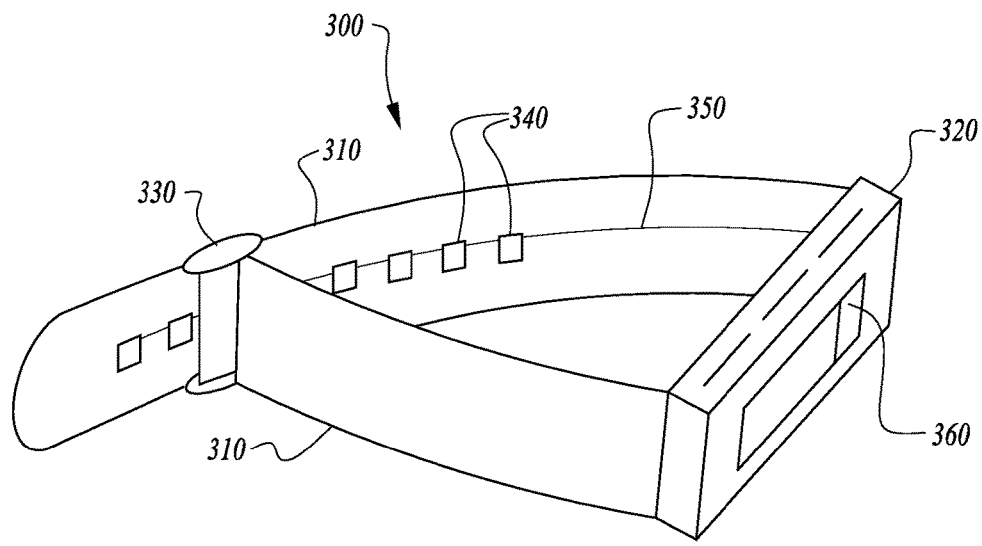
FIG. 3 illustrates an example embodiment of a system and method for generating and using a wearable device profile.
Figure 4:
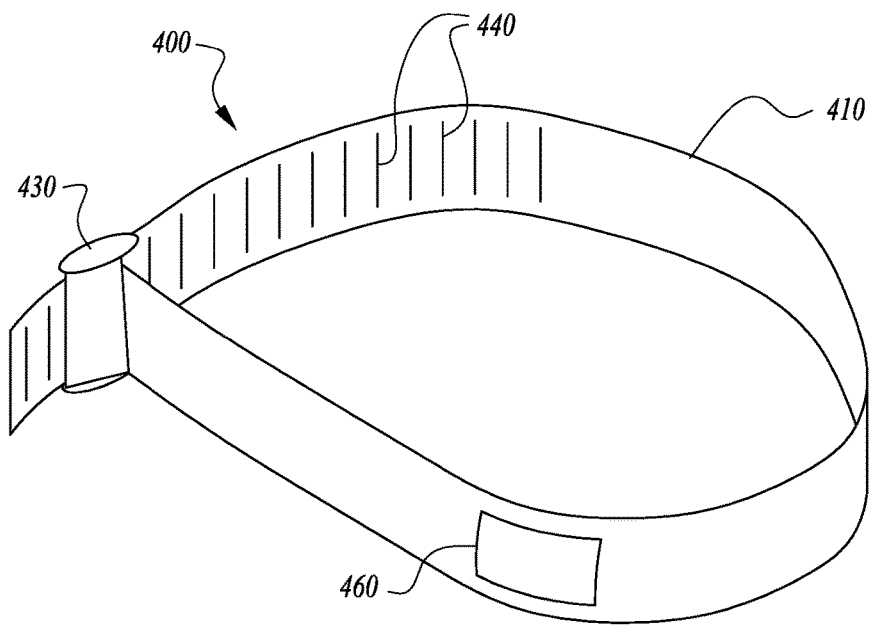
FIG. 4 illustrates another example embodiment of a system and method for generating and using a wearable device profile.

Referring now to FIGS. 3 and 4, example embodiments of a system for generating and using a wearable device profile are illustrated. These example embodiments can be used to obtain and report, for example, the circumference of the retention mechanism used to secure a mobile device to the body or other object of a user. FIG. 3 illustrates a system 300 including a wearable mobile device 320 with a connected retention mechanism including an attachment mechanism in the form of straps 310 with an adjustable clip 330 that can adjustably secure the straps 310 at various different attachment points 340 to adjust the circumference (e.g., sizing) created by the straps 310. As well-known, such an attachment mechanism can be used to attach the mobile device 320 with the connected retention mechanism to a part of the user's body or another object. The clip 330 can be configured to include a small computing element (e.g., a processor, controller, a logic, array, or the like), a memory device, and a sensing surface. The computing element and the memory device can be used to process and store data. The sensing surface of clip 330 can make electrical or magnetic contact with corresponding conductive elements installed at each of the attachment points 340. When the strap 310 is adjusted by the user, the movement of the attachment points 340 across the sensing surface of the clip 330 allows a conduction to occur between the sensing surface of the clip 330 and a particular one of the conductive elements 340 at the point where the user has secured the clip 330. The identity or location of the particular one of the conductive elements 340, and other attachment data, can be obtained by the computing element of the clip 330 and stored in the memory device of the clip 330. In this example embodiment, the retention mechanism (e.g., the combination of the attachment mechanism including the straps 310 and the clip 330, along with the computing element and the memory device) can obtain the sizing of the straps as adjusted by the user and save this sizing data in the memory device of the retention mechanism. This strap sizing data can be saved as part of a wearable device profile stored on the retention mechanism. As described in more detail below, this wearable device profile can be reported to an associated mobile device or other electronic device. In an alternative embodiment, a memory device can be installed at each of the conductive elements 340. These memory devices can be used to store an identifier corresponding to the particular conductive element 340. In another embodiment, these memory devices can be used to store an indication of the presence or absence of a conduction event or a setting value relative to the sensing surface of the clip 330.

Referring again to FIG. 3, the mobile device 320 or the associated retention mechanism can be configured to include a receptacle for a snap-in module 360. As described in more detail below, the snap-in module 360 can include a variety of sensor arrays, input and output subsystems, and data processing, data storage, and data communication capabilities. In the example embodiment shown in FIG. 3, the snap-in module 360 can be inserted into a wrist-based strap. The snap-in module 360 can receive the wearable device profile data generated and stored by the retention mechanism in a variety of ways. As shown in FIG. 3, a wired connection 350 can be used to electrically connect the retention mechanism with the snap-in module 360. In alternative embodiments, a wireless data connection can be established between the computing element of the retention mechanism and the snap-in module 360. In either case, the snap-in module 360 can receive the wearable device profile data, including the sizing data determined by the retention mechanism. This wearable device profile data can be used by the snap-in module 360 in a variety of ways to configure the operation of the associated mobile device 320. For example, the wearable device profile data, and particularly the retention mechanism sizing information, can be used to infer the particular body part or object on which the snap-in module 360 and the associated mobile device 320 is being worn. Depending on the wearable device profile data and the information on how the mobile device is being worn, the snap-in module 360 and the associated mobile device 320 can be automatically configured to behave in different ways. For example, the snap-in module 360 and/or the associated mobile device 320 can be configured to display a watch face by default if the wearable device profile data indicates that the mobile device 320 is being worn on the wrist of the user. By contrast, the snap-in module 360 and/or the associated mobile device 320 can be configured to function as a life-logging camera if the wearable device profile data indicates that the mobile device 320 is being worn as attached to a head strap. It will be apparent to one of ordinary skill in the art in view of the disclosure herein that the snap-in module 360 and/or the associated mobile device 320 can be configured to function in a variety of different ways based on information obtained or inferred from the wearable device profile data. The determination of function can be made at various points in the system. For example, the snap-in module 360 may contain a sufficient computing system, as described herein, to read the wearable device profile data from the retention mechanism and use accelerometer data, for example, differently to estimate calories burned, speed, distance traveled, etc., depending on the information obtained or inferred from the wearable device profile data. Alternatively, the snap-in module 360 can wirelessly transmit data to a smartphone and/or a cloudbased server to run code that treats accelerometer data or other sensor data differently based on the information obtained or inferred from the wearable device profile data.

Referring now to FIG. 4, an alternative embodiment of a system and method for generating and using a wearable device profile is illustrated. In the example embodiment 400 shown in FIG. 4, a retention mechanism including an attachment mechanism in the form of strap or band 410 with an adjustable clip 430 is provided. The attachment mechanism of the retention mechanism can adjustably secure the strap 410 at various different attachment points 440 to adjust the circumference (e.g., sizing) created by the strap 410. As well-known, such an attachment mechanism can be used to attach the retention mechanism to a part of the user's body or another object. The clip 430 can be configured to include a small computing element (e.g., a processor, controller, a logic, array, or the like), a memory device, and a sensing surface. The computing element and the memory device can be used to process and store data. The sensing surface of clip 430 can make electrical or magnetic contact with corresponding conductive elements installed at each of the attachment points 440. When the strap 410 is adjusted by the user, the movement of the attachment points 440 across the sensing surface of the clip 430 allows a conduction to occur between the sensing surface of the clip 430 and a particular one of the conductive elements 440 at the point where the user has secured the clip 430. The identity or location of the particular one of the conductive elements 440 can be obtained by the computing element of the clip 430 and stored in the memory device of the clip 430. In this example embodiment, the retention mechanism (e.g., the combination of the attachment mechanism including strap 410 and the clip 430, along with the computing element and the memory device) can obtain the sizing of the strap 410 as adjusted by the user and save this sizing data in the memory device of the retention mechanism. This strap sizing data can be saved as part of a wearable device profile stored on the retention mechanism. As described in more detail below, this wearable device profile can be reported to an associated mobile device or other electronic device. In an alternative embodiment, a memory device can be installed at each of the conductive elements 440. These memory devices can be used to store an identifier corresponding to the particular conductive element 440. In another embodiment, these memory devices can be used to store an indication of the presence or absence of a conduction event or a setting value relative to the sensing surface of the clip 430.

Referring again to FIG. 4, the strap 410 can be configured to include a receptacle for an accelerometer 460 or other sensing device. As well known in the art, such sensing devices 460 can be configured to wirelessly report sensor data to a separate mobile device or proximate computing device. In a similar manner, the retention mechanism can wirelessly report the wearable device profile data, including strap 410 sizing data, to a separate mobile device, a proximate computing device, or other electronic device. The separate mobile device or proximate computing device can use the wearable device profile data to configure the processing of the sensor data received from the sensing device 460. For example, as described above, the separate mobile device or proximate computing device can use the accelerometer data differently to estimate calories burned, speed, distance traveled, etc., depending on the information obtained or inferred from the wearable device profile data. Additionally, the separate mobile device or proximate computing device can be configured to function in a variety of different ways or modes based on information obtained or inferred from the wearable device profile data received from the retention mechanism.

In an example embodiment, the wearable device profile data obtained, retained, or inferred by the retention mechanism of various example embodiments described herein can include one or more of the following data fields or values: 1) retention mechanism type, 2) wearable vs. non-wearable device, 3) previous retention mechanism size settings, 4) current retention mechanism size setting, 5) various body part measurements provided by the user/owner that be correlated with the retention mechanism sizing data to determine the body part that corresponds to the retention mechanism size setting, 6) object types to which the retention mechanism can be attached, 7) various object part measurements provided by the user/owner that be correlated with the retention mechanism sizing data to determine the object part that corresponds to the retention mechanism size setting, 8) user/owner demographic information, 9) default configuration data, and related data. Some of the wearable device profile data may be populated by default during manufacture or provided through system updates. The first time a user/owner wears a mobile device with the retention mechanism on a given body part, the user/owner can indicate to the retention mechanism to which part of the body the retention mechanism is attached using a user interface (e.g., voice input/output—I/O, a phone app user interface—UI, or the like). Subsequently, the retention mechanism can make that determination automatically based on the detected retention mechanism size setting and the corresponding body part or object. In the case of accelerometer readings, the mobile device can use the wearable device profile data provided by the retention mechanism of an example embodiment to configure the accelerometer data as coming from the wrist or the ankle, for example.

Figure 5:
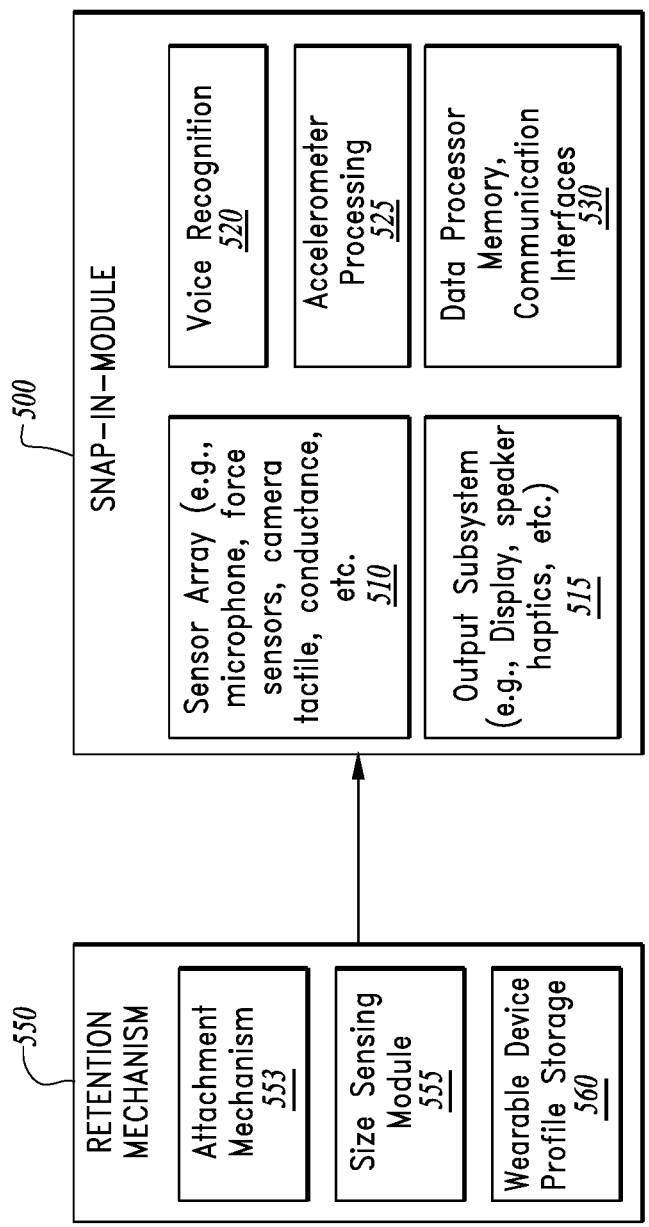
FIG. 5 illustrates the system components of an example embodiment of a retention mechanism and a snap-in module.

FIG. 5 illustrates the system components of an example embodiment of the retention mechanism 550 and the snap-in module 500. As described above for an example embodiment, the retention mechanism 550 can be configured to be in data communication with the snap-in module 360 in either a wired or wireless configuration. The retention mechanism 550 in an example embodiment can include an attachment mechanism 553, a size sensing or sensing module 555, and a memory element 560 for storage of the wearable device profile data, including the sizing data. The attachment mechanism 553 can include the straps or band and the clip as described above. The size sensing or sensing module 555 can include a small computing element (e.g., a processor, controller, a logic, array, or the like) and one or more sensing surfaces. In an example embodiment, the size sensing module 555 can be installed in a clip or other portion of the attachment mechanism 553 of the retention mechanism 550. The size sensing module 555 can be used to process the attachment data received from the conductive elements of a strap or band of the retention mechanism 550. As described above, when the strap or band is adjusted by the user, the movement of the attachment points on the strap or band across the sensing surface of the clip allows the size sensing module 555 to identify or locate the particular one of the attachment points at which the strap or band has been secured. This information can be obtained by the size sensing module 555 and stored in the memory element 560 with the wearable device profile data. As a result, the retention mechanism 550 can obtain the sizing of the straps or band as adjusted by the user and can save this sizing data in the memory element 560 of the retention mechanism 550. The computing element of the size sensing module 555 can report this wearable device profile to the snap-in module 500 in a wired or wireless data communication as described above.

Referring still to FIG. 5, the snap-in module 500 of an example embodiment can include a variety of sensor arrays 510, output subsystems 515, input subsystems 520 and 525, and data processing, data storage, and data communication capabilities 530. In a particular embodiment, the sensor arrays 510 can include microphones, force detectors, cameras, tactile sensors, conductance sensors, and a variety of other sensing devices. The output subsystems 515 can include display devices, speakers, haptic devices, and other output devices. The input subsystems can include a voice recognition module 520 and an accelerometer processing module 525. The voice recognition module 520 can be used to receive voice input from a user for configuration of the retention mechanism 550 and/or the snap-in module 500. The accelerometer processing module 525 can be used to process accelerometer data received from an accelerometer or acceleration sensor. The component 530 can include a data processor, a memory device, and communication interfaces for communicating with the retention mechanism 550 and/or separate mobile devices or other computing systems.

In the example embodiment shown in FIG. 5, the snap-in module 500 can receive the wearable device profile data generated and stored by the retention mechanism 550 in a variety of ways. As shown in FIG. 3 and described above, a wired connection can be used to electrically connect the retention mechanism 550 with the snap-in module 500. In alternative embodiments, a wireless data connection can be established between the retention mechanism 550 and the snap-in module 500. In either case, the snap-in module 500 can receive the wearable device profile data, including the sizing data determined by the retention mechanism 550. This wearable device profile data can be used by the snap-in module 500 in a variety of ways to configure the operation of the sensor arrays 510, the output subsystems 515, the input subsystems 520 and 525, and/or an associated mobile device. For example, the wearable device profile data, and particularly the retention mechanism sizing information, can be used to infer the particular body part or object on which the snap-in module 500 and the associated mobile device are being worn or attached. Depending on the wearable device profile data and the information on how the mobile device is being worn or attached, the snap-in module 500 and the associated mobile device can be automatically configured to behave in different ways. For example, if the wearable device profile data indicates that the snap-in module 500 and the associated mobile device are being worn on the wrist of the user, the snap-in module 500 and/or the associated mobile device can be configured to, for example, activate (or deactivate) a tactile or conductance sensor of sensor arrays 510, deactivate (or activate) a camera of sensor arrays 510, display a watch face via output subsystems 515, adjust the accelerometer processing module 525 for a wrist-worn sensor, and the like. In other examples, the snap-in module 500 and/or the associated mobile device can be configured to activate a camera of sensor arrays 510 to function as a life-logging camera, if the wearable device profile data indicates that the snap-in module 500 and/or the associated mobile device is being worn as attached to a head strap. It will be apparent to one of ordinary skill in the art in view of the disclosure herein that the snap-in module 500 and/or the associated mobile device can be configured to function in a variety of different ways based on information obtained or inferred from the wearable device profile data. In other examples, the snap-in module 500 and/or the associated mobile device can be configured to cause the accelerometer processing module 525 to use accelerometer data differently to estimate calories burned, speed, distance traveled, etc., depending on the information obtained or inferred from the wearable device profile data. In yet another embodiment, the wearable device profile may be stored in part on the snap-in module 500 and in part on the retention mechanism 550 and/or on separate mobile devices or other computing systems. In this case, the retention mechanism 550 may, for example, just report the identity of the body part to which the retention mechanism 550 is attached. Then, the snap-in module 500 can direct device behavior that corresponds to the identified body part.

It will be apparent to one of ordinary skill in the art in view of the disclosure herein that various parts of the snap-in module 500 as described herein can be optional and/or located on a device separate from the illustrated snap-in module 500, including output subsystem 515, voice recognition module 520, and accelerometer processing module 525. It will also be apparent to those of ordinary skill in the art in view of the disclosure herein that a variety of different configurations of the system components as described herein can be implemented.

Figure 6:
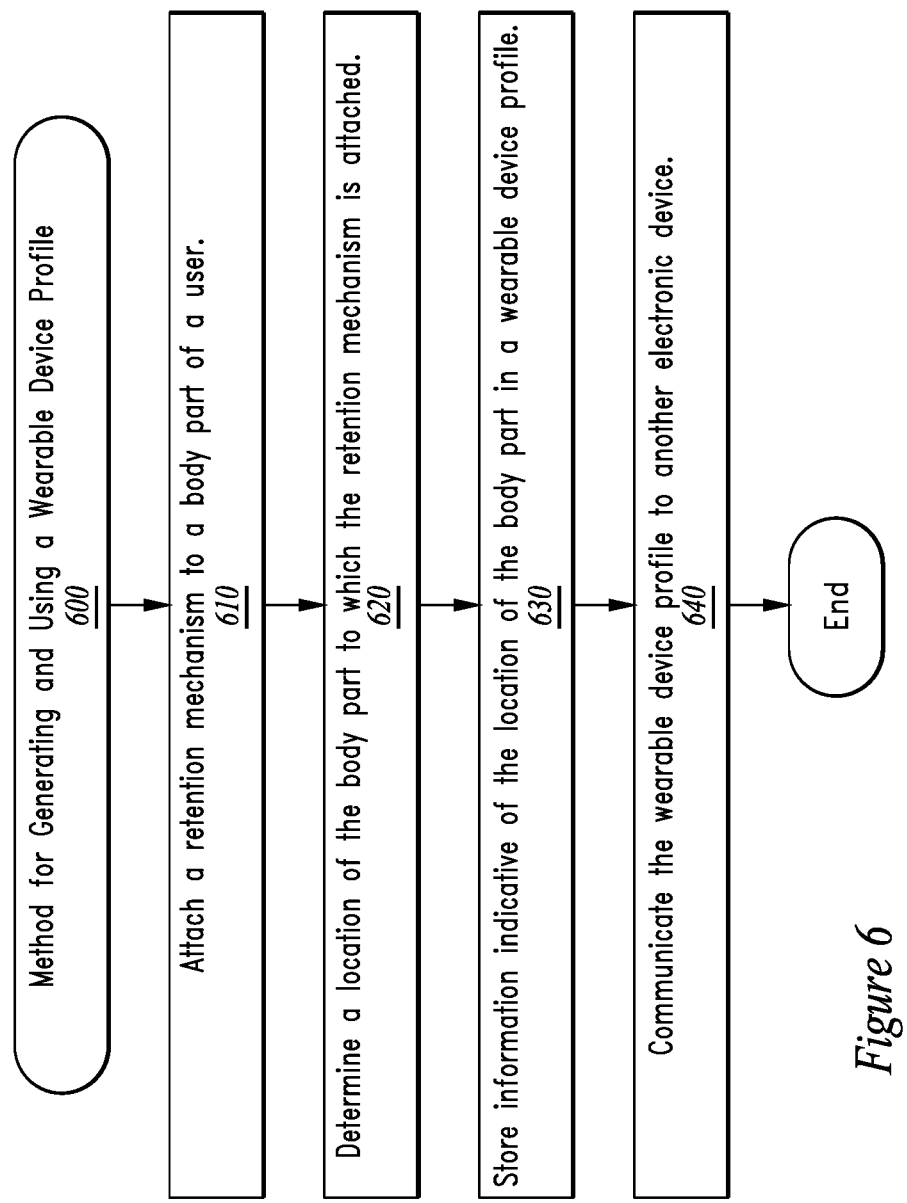
FIG. 6 is a flow chart illustrating an example embodiment of a method as described herein.

Referring now to FIG. 6, a flow diagram illustrates an example embodiment of a method for generating and using a wearable device profile as described herein. The method 600 of an example embodiment includes: attaching a retention mechanism to a body part of a user (processing block 610); determining a location of the body part to which the retention mechanism is attached (processing block 620); storing information indicative of the location of the body part in a wearable device profile (processing block 630); and communicating the wearable device profile to another electronic device (processing block 640).

Figure 7:
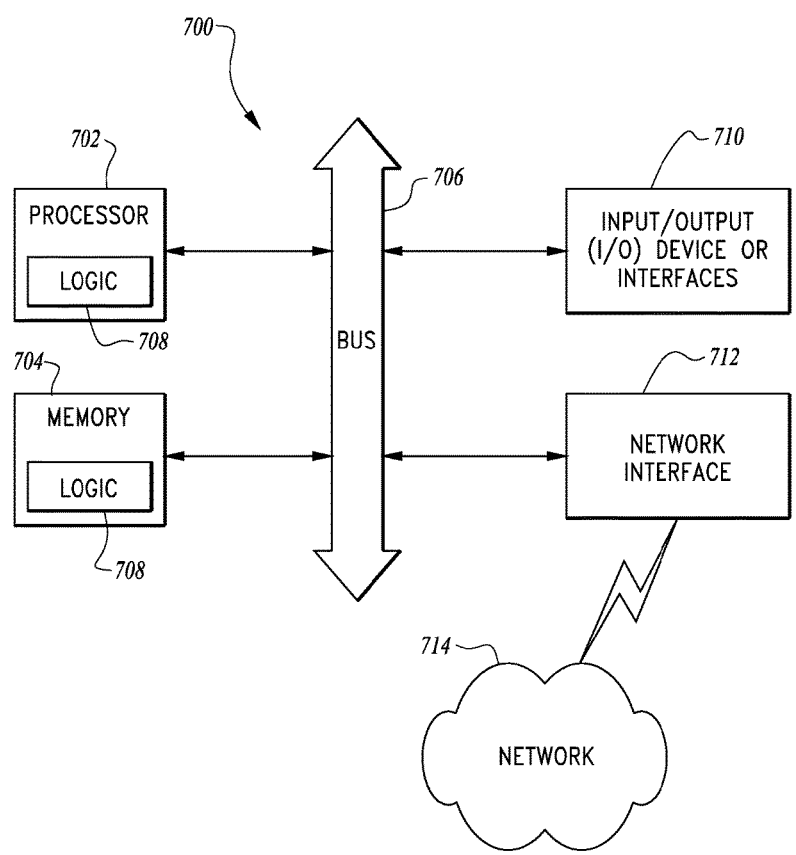
FIG. 7 shows a diagrammatic representation of a machine in the example form of a mobile computing and/or communication system within which a set of instructions when executed and/or processing logic when activated may cause the machine to perform any one or more of the methodologies described and/or claimed herein.

FIG. 7 shows a diagrammatic representation of a machine in the example form of a mobile computing and/or communication system 700 within which a set of instructions when executed and/or processing logic when activated may cause the machine to perform any one or more of the methodologies described and/or claimed herein. In alternative embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a personal computer (PC), a laptop computer, a tablet computing system, a Personal Digital Assistant (PDA), a cellular telephone, a smartphone, a web appliance, a set-top box (STB), a network router, switch or bridge, or any machine capable of executing a set of instructions (sequential or otherwise) or activating processing logic that specify actions to be taken by that machine. Further, while only a single machine is illustrated, the term "machine" can also be taken to include any collection of machines that individually or jointly execute a set (or multiple sets) of instructions or processing logic to perform any one or more of the methodologies described and/or claimed herein.

The example mobile computing and/or communication system 700 includes a data processor 702 (e.g., a System-on-a-Chip (SoC), general processing core, graphics core, and optionally other processing logic) and a memory 704, which can communicate with each other via a bus or other data transfer system 706. The mobile computing and/or communication system 700 may further include various input/output (I/O) devices and/or interfaces 710, such as a touchscreen display, an audio jack, and optionally a network interface 712. In an example embodiment, the network interface 712 can include one or more radio transceivers configured for compatibility with any one or more standard wireless and/or cellular protocols or access technologies (e.g., 2nd (2G), 2.5, 3rd (3G), 4th (4G) generation, and future generation radio access for cellular systems, Global System for Mobile communication (GSM), General Packet Radio Services (GPRS), Enhanced Data GSM Environment (EDGE), Wideband Code Division Multiple Access (WCDMA), LTE, CDMA2000, WLAN, Wireless Router (WR) mesh, and the like). Network interface 712 may also be configured for use with various other wired and/or wireless communication protocols, including TCP/IP, UDP, SIP, SMS, RTP, WAP, CDMA, TDMA, UMTS, UWB, WiMax, Bluetooth, IEEE 802.11x, and the like. In essence, network interface 712 may include or support virtually any wired and/or wireless communication mechanisms by which information may travel between the mobile computing and/or communication system 700 and another computing or communication system via network 714.

The memory 704 can represent a machine-readable medium on which is stored one or more sets of instructions, software, firmware, or other processing logic (e.g., logic 708) embodying any one or more of the methodologies or functions described and/or claimed herein. The logic 708, or a portion thereof, may also reside, completely or at least partially within the processor 702 during execution thereof by the mobile computing and/or communication system 700. As such, the memory 704 and the processor 702 may also constitute machine-readable media. The logic 708, or a portion thereof, may also be configured as processing logic or logic, at least a portion of which is partially implemented in hardware. The logic 708, or a portion thereof, may further be transmitted or received over a network 714 via the network interface 712. While the machine-readable medium of an example embodiment can be a single medium, the term "machine-readable medium" should be taken to include a single non-transitory medium or multiple non-transitory media (e.g., a centralized or distributed database, and/or associated caches and computing systems) that store the one or more sets of instructions. The term "machine-readable medium" can also be taken to include any non-transitory medium that is capable of storing, encoding or carrying a set of instructions for execution by the machine and that cause the machine to perform any one or more of the methodologies of the various embodiments, or that is capable of storing, encoding or carrying data structures utilized by or associated with such a set of instructions. The term "machine-readable medium" can accordingly be taken to include, but not be limited to, solid-state memories, optical media, and magnetic media.

In various embodiments as described herein, example embodiments include at least the following examples.

A retention mechanism comprising: an attachment mechanism configured to attach the retention mechanism to a body part of a user; a memory device for storage of information indicative of a location of the body part in a wearable device profile; and a data interface for communicating the wearable device profile to another electronic device.

The retention mechanism as claimed above including a sensing module to determine the location of the body part to which the retention mechanism is attached.

The retention mechanism as claimed above including a sensing module to determine the location of the body part to which the retention mechanism is attached, the sensing module including a computing element to determine a sizing of the attachment mechanism as adjusted by the user.

The retention mechanism as claimed above wherein the attachment mechanism includes one or more straps or a band and a clip to adjustably secure the straps or the band at a particular attachment point.

The retention mechanism as claimed above wherein the information indicative of the location of the body part includes information corresponding to a sizing of the attachment mechanism as adjusted by the user.

The retention mechanism as claimed above including a snap-in module in data communication with the data interface.

The retention mechanism as claimed above wherein the data interface for communicating the wearable device profile is configured to communicate the wearable device profile via a wired or wireless data connection.

A system comprising: a mobile device; and a retention mechanism including an attachment mechanism configured to attach the retention mechanism and the mobile device to a body part of a user; a memory device for storage of information indicative of the location of the body part in a wearable device profile; and a data interface for communicating the wearable device profile to another electronic device.

The system as claimed above including a sensing module to determine the location of the body part to which the retention mechanism is attached.

The system as claimed above including a sensing module to determine the location of the body part to which the retention mechanism is attached, the sensing module including a computing element to determine a sizing of the attachment mechanism as adjusted by the user.

The system as claimed above wherein the attachment mechanism includes one or more straps or a band and a clip to adjustably secure the straps or the band at a particular attachment point.

The system as claimed above wherein the information indicative of the location of the body part includes information corresponding to a sizing of the attachment mechanism as adjusted by the user.

The system as claimed above including a snap-in module in data communication with the data interface.

The system as claimed above wherein the data interface for communicating the wearable device profile is configured to communicate the wearable device profile via a wired or wireless data connection.

The system as claimed above wherein the mobile device is of a type from the group consisting of: a Personal Digital Assistant (PDA), a cellular telephone, a smartphone, a web appliance, a fitness device, a medical device, a timing device, a communication device, and a recording device.

A method comprising: attaching a retention mechanism to a body part of a user; determining a location of the body part to which the retention mechanism is attached; storing information indicative of the location of the body part in a wearable device profile; and communicating the wearable device profile to another electronic device.

The method as claimed above including using one or more straps or a band and a clip to adjustably secure the straps or the band at a particular attachment point.

The method as claimed above including determining a sizing of an attachment mechanism as adjusted by the user.

The method as claimed above including communicating with a snap-in module.

The method as claimed above including communicating the wearable device profile via a wired or wireless data connection.

A non-transitory machine-useable storage medium embodying instructions which, when executed by a machine, cause the machine to: attach a retention mechanism to a body part of a user; determine a location of the body part to which the retention mechanism is attached; store information indicative of the location of the body part in a wearable device profile; and communicate the wearable device profile to another electronic device.

The machine-useable storage medium as claimed above being further configured for use of one or more straps or a band and a clip to adjustably secure the straps or the band at a particular attachment point.

The machine-useable storage medium as claimed above being further configured to determine a sizing of an attachment mechanism as adjusted by the user.

The machine-useable storage medium as claimed above being further configured to communicate with a snap-in module.

The machine-useable storage medium as claimed above being further configured to communicate the wearable device profile via a wired or wireless data connection.

An apparatus comprising: an attachment means configured to attach the apparatus to a body part of a user; a memory means for storage of information indicative of a location of the body part in a wearable device profile; and a data interfacing means for communicating the wearable device profile to another electronic device.

The apparatus as claimed above including a sensing means to determine the location of the body part to which the apparatus is attached.

The apparatus as claimed above including a sensing means to determine the location of the body part to which the apparatus is attached, the sensing means including a computing means to determine a sizing of the attachment means as adjusted by the user.

The apparatus as claimed above wherein the attachment means includes one or more straps or a band and a clip to adjustably secure the straps or the band at a particular attachment point.

The apparatus as claimed above wherein the information indicative of the location of the body part includes information corresponding to a sizing of the attachment means as adjusted by the user.

The apparatus as claimed above including a snap-in means in data communication with the data interfacing means.

The apparatus as claimed above wherein the data interfacing means for communicating the wearable device profile is configured to communicate the wearable device profile via a wired or wireless data connection.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A wearable device comprising:
   a strap to attach the wearable device to a body part of a user;
   a sensor to sense an amount of the strap encircling the body part;
   at least one processor to identify the body part based on the amount of the strap sensed by the sensor;
   a memory to store information identifying the body part; and
   a data interface to export the information identifying the body part.

2. The wearable device of claim 1, further including a clip to adjust the amount of the strap encircling the body part.

3. The wearable device of claim 2, wherein the strap includes a plurality of attachment points, the clip adjustably securable to different ones of the attachment points to adjust the amount of the strap encircling the body part.

4. The wearable device of claim 3, wherein the clip includes the sensor, and further including a plurality of conductors located at respective ones of the attachment points, the sensor including a surface to close a circuit via at least one of the conductors.

5. The wearable device of claim 4, wherein the at least one processor is to determine the amount of the strap encircling the body part based on the circuit including the sensor and the at least one of the conductors.

6. The wearable device of claim 4, further including a plurality of identifier memories associated with respective ones of the conductors.

7. The wearable device of claim 6, wherein the identifier memories store respective identifiers corresponding to the respective conductors.

8. The wearable device of claim 6, wherein the identifier memories store indications of a presence or an absence of a conduction event associated with the respective conductors.

9. The wearable device of claim 1, further including an accelerometer carried by the strap to obtain acceleration data.

10. The wearable device of claim 9, wherein the at least one processor is to analyze the acceleration data based on the information identifying the body part.

11. The wearable device of claim 1, wherein the at least one processor is to identify the body part further based on sizing information associated with body parts of the user as previously established via a user interface of the wearable device, the sizing information saved in the memory.

12. A machine-readable memory comprising instructions that, when executed, cause a machine to at least:
   determine a circumference of a body part of a user based on an interaction of a clip of a strap carrying a wearable device and a corresponding one of a plurality of conductive attachment points;
   identify the body part based on the circumference; and
   change an operation of the wearable device based on the body part.

13. The machine-readable memory of claim 12, wherein the instructions, when executed, cause the machine to change the operation of the wearable device by at least one of activating or deactivating a tactile or conductive sensor, activating or deactivating a camera, changing a display, or adjusting an accelerometer.

14. The machine-readable memory of claim 12, wherein the instructions, when executed, cause the machine to change the operation of the wearable device by changing a calculation of at least one of calories burned, distance traveled, or speed.

15. The machine-readable memory of claim 12, wherein the strap includes the plurality of conductive attachment points, and the strap is adjustable around the body part via the clip carried by the strap.

16. The machine-readable memory of claim 12, wherein respective ones of the conductive attachment points are associated with storage including identifiers corresponding to respective ones of the conductive attachment points.

17. The machine-readable memory of claim 12, wherein the instructions, when executed, cause the machine to identify the body part by comparing the circumference to a list of body parts and corresponding circumferences associated with the body parts.

18. A wearable device comprising:
means for retaining the wearable device on a body part of a user;
means for adjusting a size of the means for retaining;
means for determining sizing information of the means for retaining; and
means for identifying the body part based on the sizing information.

19. The wearable device of claim 18, further including means for sensing one or more parameters of the user, and further including means for changing a calculation using the one or more parameters based on the sizing information.

20. The wearable device of claim 18, further including means for outputting information, the means for identifying to change an operation of the means for outputting based on the sizing information.

* * * * *